United States Patent [19]

Thorne et al.

[11] Patent Number: 4,985,055
[45] Date of Patent: Jan. 15, 1991

[54] LIQUID/GAS SEPARATION DEVICE

[75] Inventors: Jonathan O. Thorne, Englewood; Christopher T. Crowley, Aurora, both of Colo.

[73] Assignee: The BOC Group, Inc., New Providence, N.J.

[21] Appl. No.: 408,647

[22] Filed: Sep. 18, 1989

Related U.S. Application Data

[63] Continuation-in-part of Ser. No. 287,707, Dec. 19, 1988, abandoned, which is a continuation of Ser. No. 71,104, Jul. 7, 1987, abandoned.

[51] Int. Cl.$^5$ .............................................. B01D 19/00
[52] U.S. Cl. .................................... 55/189; 55/159; 55/270
[58] Field of Search ............. 55/16, 55, 158, 159, 55/189, 270; 73/23.1

[56] References Cited

U.S. PATENT DOCUMENTS

| | | | |
|---|---|---|---|
| 4,268,279 | 5/1981 | Shindo et al. | 55/16 |
| 4,325,715 | 4/1982 | Bowman et al. | 55/159 X |
| 4,382,806 | 5/1983 | Hakala et al. | 55/18 |
| 4,446,869 | 5/1984 | Knodle | 128/716 |
| 4,459,844 | 7/1984 | Burkhart | 55/16 X |
| 4,461,328 | 7/1984 | Kenney | 55/159 X |
| 4,469,495 | 9/1984 | Hiraizumi et al. | 55/159 X |
| 4,473,473 | 9/1984 | Cheng | 55/16 X |
| 4,529,419 | 7/1985 | Perl et al. | 55/159 X |
| 4,558,708 | 12/1985 | Labuda et al. | 128/719 |
| 4,558,709 | 12/1985 | Aida et al. | 128/719 |
| 4,600,412 | 7/1986 | Liston et al. | 55/189 |
| 4,729,773 | 3/1988 | Shirato et al. | 55/159 X |
| 4,787,921 | 11/1988 | Shibata et al. | 55/159 |
| 4,828,587 | 5/1989 | Baurmeister et al. | 55/159 |

FOREIGN PATENT DOCUMENTS

| | | | |
|---|---|---|---|
| 2907188 | 8/1979 | Fed. Rep. of Germany | 55/159 |
| 48104 | 3/1985 | Japan | 55/159 |
| 2204399A | 11/1988 | United Kingdom . | |

OTHER PUBLICATIONS

Gore-Tex Expanded PTFE, W. L. Gore and Associates, Inc., 1983.

*Primary Examiner*—Robert Spitzer
*Attorney, Agent, or Firm*—David M. Rosenblum,; Roger M. Rathbun; Larry R. Cassett

[57] ABSTRACT

A water separator is disclosed and which is specially suited for withdrawing dry gas from liquid/gas from a patient's exhalation for analysis thereof. The separator utilizes a conduit constructed of a gas permeable material, preferably expanded polytetrafluoroethylene, surrounded by a cylindrical, annular chamber. As the liquid/gas flows through the conduit at a predetermined flow, a negative pressure differential is created between the annular chamber and the conduit to draw the dry gas through the gas permeable material. The conduit is subject to radial expansion upon the patient's exhalation and the annular chamber has a predetermined minimum diameter that is sufficient to allow the conduit to expand without contact between the conduit and an inner surface forming the chamber. The minimum diameter also minimizes the volume of the annular chamber to resist the formation of dead air spaces in the annular chamber. Additionally, since the conduit may be formed with a pre-existing curvature, such as by poltetrafluoroethylene tubing unwound from a spool, the conduit may be subjected to a tensile preload force to eliminate the pre-existing curvature. Additionally, a seal is provided between the conduit and the cylindrical chamber at the ends thereof. The seal may comprise potting material formed by an epoxy which also may serve to maintain the conduit loaded with the tensile pre-load force.

4 Claims, 1 Drawing Sheet

LIQUID/GAS SEPARATION DEVICE

RELATED PATENT APPLICATIONS

This is a continuation-in-part of application Ser. No. 287,707, filed Dec. 19, 1988, now abandoned, which was a continuation of application Ser. No. 071,104, filed Jul. 7, 1987, now abandoned.

BACKGROUND OF THE INVENTION

There are various water separators in use today that are specifically utilized in medical applications where a sample of the patient's exhalation is desired for analysis of the various constituents in such exhaled gases. Such water separators are necessary since the exhaled gases contain liquids from the patient and such liquids must be removed or in some way isolated so that only dry gas is seen by the gas analyzer.

Typical of such water separators are disclosed in U.S. Pat. No. 4,558,708 of Aida et al.; U.S. Pat. No. 4,558,709 of Labuda et al.; U.S. Pat. No. 4,600,412 of Liston et al.; U.S. Pat. No. 4,446,869 of Knodle and U.S. Pat. No. 4,382,806 of Hakala et al.

Such prior art separators employ various means of removing the liquid including filters, centrifuging, liquid sumps and the like, however, each type has various drawbacks in actual use.

The use of filters produces a separator susceptible to clogging and the inability to handle streams that, at times, may be 100% liquid. Dealing with exhaled gases from a patient, in which the gases may contain highly viscous liquids (such as mucous and saliva), is particularly difficult due to plugging of lines and/or filters by said liquids. Also, the passageways used to handle sampling of exhaled gases are small so as to take only a minute sample from the patient circuit. In addition, filters require constant attention for replacement, cleaning or disposal.

In the filter means of Labuda et al., for example, a hydrophobic baffle is directly in the patient circuit adjacent the mouthpiece and the main flow therethrough is bidirectional, that is, the flow reverses direction as the patient inhales and exhales. There is no means to continually draw that main stream through the baffle and thus, the baffle collects the liquid materials and needs to be constantly monitored and replaced since it is obviously not desirable to draw that liquid through the patient circuit to enter the patients airway or mask.

Centrifuges require of course, moving parts and thus are costly and relatively difficult to manufacture.

Liquid sumps generally pass the liquid/gas through a large reservoir where the liquid is drawn off the bottom and the dry air removed from the top of the reservoir. Such devices have fairly large dead air space and thus, the constituents in previous exhalations admitted to the reservoirs can affect the accuracy. Also, dead air space affects the wave form to the constituent monitors by increasing the response time, thus modifying the actual wave form.

SUMMARY OF THE INVENTION

In accordance with this invention, a water separator is provided to remove liquid and thereby to draw dry gas from a patient's exhalation for analysis of the dry gas in a gas analyzer.

The separator is simple in construction, resists the formation of dead air spaces and allows the flow of exhalant to continue unimpeded while the dry gas is drawn therefrom.

The water separator of the present invention includes means having an inlet for receiving the patient's exhalation, a liquid outlet for discharging the removed liquid, and a conduit communicating between the inlet and the liquid outlet. The conduit is formed of a porous material permeable to gas, but impermeable to liquid for allowing the dry gas to pass through the porous material and for causing the liquid to collect in the conduit for discharge through the liquid outlet. Chamber means are also provided having an inner surface forming a cylindrical, annular chamber around the conduit for collecting the dry gas passed through the porous material and a gas outlet for discharging the dry gas to the breath gas analyzer. Additionally, means establishing a negative pressure differential between the cylindrical chamber and the inside of said the conduit means are provided for drawing the patient's exhalation through the inlet, for drawing the dry gas through the porous material and out of the gas outlet, and for drawing the collected liquid out of the liquid outlet.

The ratio of the outer diameter of the conduit and the diameter of the cylindrical chamber should preferably approach 1 to minimize the formation of dead air space between the conduit and the inner surface forming the cylindrical chamber. However, the conduit is subject to radial expansion upon the patient's exhalation; and therefore, the closer such ratio is to 1, the more likely that radial expansion may result in contact between the conduit means and the inner surface of the chamber means and, thus, obstruction of the annular chamber. If the annular chamber is entirely obstructed, then dry gas will not be drawn through the conduit. If the annular chamber is partially obstructed, then the conduit will only be partially subjected to the negative pressure differential, to one side of such partial obstruction. Such obstruction thus reduces the effective length of the conduit for the transfer of dry gas to the cylindrical chamber. This reduced effective length may result in the eventual clogging of the conduit by the more viscous liquid components of the patient's exhalant, such as mucus or blood. As a result, the annular chamber, in accordance with one aspect of the present invention, has a predetermined, minimum diameter sufficient to allow the conduit to expand without contact between the conduit and the inner surface of the chamber means for preventing obstruction of the annular chamber by the conduit. Since, the diameter is at a minimum, the volume of the annular chamber less that of the conduit is also at a minimum to resist the formation of dead air space between the conduit and the inner surface forming the annular chamber.

In accordance with another aspect of the present invention, the conduit has a pre-existing curvature. For instance, the conduit may be formed by polytetrafluoroethylene tubing. Often such tubing is rolled onto a spool for storage and/or for sale. When the tubing is unrolled from the spool, a slight curvature may be found to have been imparted to the tubing. In such case, in order to maintain the clearance between the conduit and the inner surface forming the annular chamber, the conduit has an applied tensile preload force to eliminate the pre-existing curvature and the sealing means, mentioned above, also function to maintain such tensile preload force on the conduit.

As set forth above, preferably an expanded polytetrafluoroethylene (PTFE) tube is used in the formation of the conduit. Such tubing is readily available commercially from W. L. Gore & Associates, Inc. under the trademark GORTEX in various pore sizes and dimensions. One can readily select the particular material from known specifications as to pore size, flow, pressure or vacuum levels etc.

Thus, very small dead air space is present that could effect the accuracy and wave form of the gas analysis of the sample taken and yet the device is efficient and readily manufacturable with little difficulty.

The foregoing and other advantages and features of the present invention will become readily apparent from the following description.

BRIEF DESCRIPTION OF THE DRAWINGS

The invention is diagrammatically illustrated by way of examples in the drawings appended hereto, in which.

DESCRIPTION OF THE PREFERRED EMBODIMENT

Figure 1:
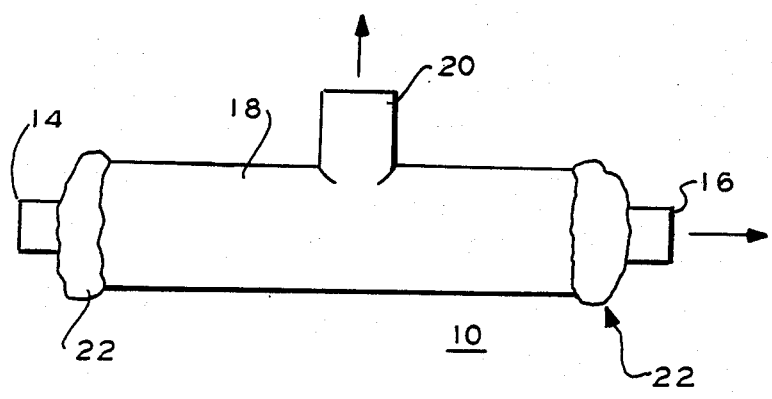
FIG. 1, is a front view of the liquid/gas separator of the present invention.
Figure 2:
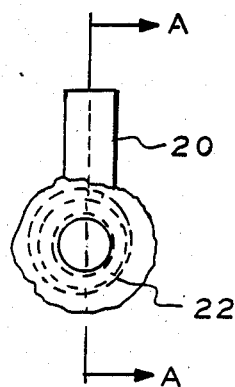
FIG. 2, is an end view of the separator of FIG. 1.

Referring now to FIGS. 1 and 2, there is shown a front view and an end view of the liquid/gas separator 10 having an inlet 14 and an outlet 16.

Inlet 14 receives the liquid containing gas from the exhalation of a patient. Typically, at or near the patient, a minute tubing is attached to the patient circuit and vacuum is utilized to withdraw a sample of exhaled gases for analysis of gas constituents such as $CO_2$ and $O_2$. Since the electronic instruments that analyze such gases require a dry gas, it is therefore necessary to remove dry gas for analysis from the stream withdrawn from the patients exhalation and which normally contains highly viscous liquids. A cylindrical jacket 18 is provided spanning inlet 14 and outlet 16 and has a gas outlet 20 formed therein. As will be explained, dry gas is drawn from the gas outlet 20 to be directed to gas instrumentation for analysis of its components.

A potting material 22 is used to seal the ends of cylindrical jacket 18 around inlet 14 and outlet 16 as seen in both FIGS. 1 and 2.

Figure 3:
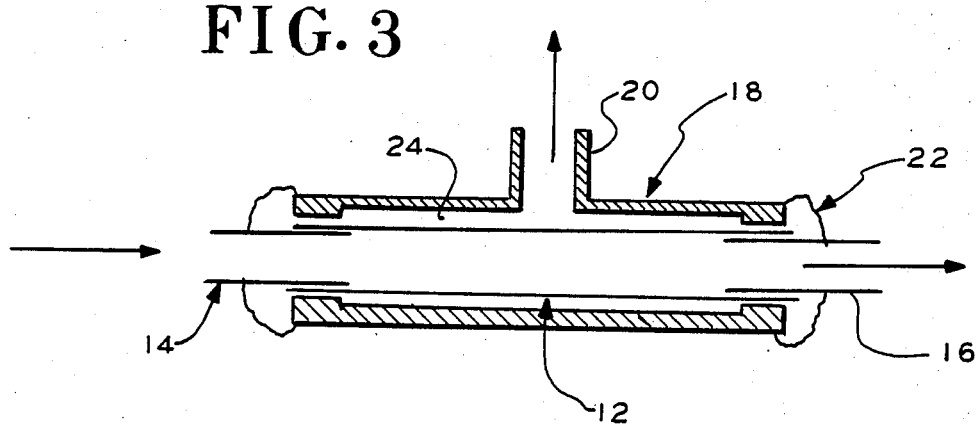
FIG. 3, is a cross-sectional view taken along the lines A—A of FIG. 2.

Turning now to FIG. 3, there is shown a cross-sectional view of the liquid/gas separator 10 taken along the line A—A of FIG. 2. As can be seen in FIG. 3, a conduit 12 is positioned between inlet 14 and outlet 16 such that fluids entering the inlet 14 from the patient circuit pass through conduit 12 before exiting through outlet 16. Conduit 12 is a tube formed of the gas permeable material and the particular material is selected depending upon the pressures, flows and liquid/gas composition. Preferably, inlet 14 and outlet 16 are formed by a pair of stainless steel end tubes tightly fitted within the ends of conduit 12. A cylindrical annular chamber 24 is formed around conduit 12 by cylindrical jacket 18. As illustrated, chamber 24 is the volume between the inner surface of jacket 18 and the outer surface of conduit 12. The potting material 22 may be epoxy and serves to seal the inlet 14 and outlet 16 to the conduit 12 to prevent liquid from being drawn into annular chamber 24. It also seals inlet 14 and outlet 16 within cylindrical jacket 18, thus preventing ambient air from being drawn into conduit 12 or annular chamber 24. Due to the difficulty of obtaining a good seal about PTFE, a mechanical seal or clamp may also be used. It is possible to delete the steel end tubes forming inlet 14 and outlet 16 by increasing the length of conduit 12 so that the ends of conduit 12 protrude from the ends of jacket 18 to form an inlet and an outlet of conduit 12 and by bonding the ends of such a lengthened conduit 12, by epoxy, to cylindrical jacket 18. A vacuum means (not shown) is connected to gas outlet 20 such that the annular chamber 24 is established at the desired slight vacuum. The slight vacuum of annular chamber 24 is predetermined in accordance with the flow and other characteristics of the separator.

As a design criteria, the amount of vacuum is determined so that the differential pressure between the inside of conduit 12 and annular chamber 24 (or the outside of conduit 12) is within the limits established for the particular pore size incorporated into the material utilized for forming conduit 12. If the pore size is extremely small, a higher differential pressure can be tolerated. Ultimately, if the differential pressure across the wall of conduit 12 is too high, liquid will be drawn through the wall and disrupt the system. That same vacuum source can be utilized to draw the main stream of liquid/gas through the liquid/gas separator 10 by connection (not shown) to outlet 14 but the levels of vacuum for the different purposes may vary.

The level of the vacuum used to draw dry gas through conduit 12 can be predetermined and established depending upon the particular material used for the gas permeable wall. The flow of the liquid/gas can be established by adjusting the vacuum level used to draw that main stream through the liquid/gas separator 10. Preferably, the latter source of vacuum is variable, either manually or automatically, such that it can be increased in the event an excess of liquid is flowing through liquid/gas separator 10 to increase the flow to pull that liquid therethrough. An automatic means could comprise a gas flow detector that senses when the gas withdrawn by gas outlet 20 is below a predetermined flow, thus indicating that excessive liquid is passing through conduit 12. The gas flow detector could then automatically cause an increase in the vacuum level used to draw the main liquid/gas stream through conduit 12 to pull the excess liquid through until the predetermined flow of dry gas is again detected by the gas flow sensor.

The liquids drawn from outlet 16 can be collected in a collection bottle or trap (not shown) for periodic removal. As the liquid/gas therefore flows continuously and unimpeded between inlet 14 and outlet 16, the predetermined vacuum in annular chamber 24 draws the dry gas contained in the liquid/gas through the gas permeable walls of conduit 12.

Thus, even where 100% liquid passes through conduit 12, flow can move continuously since there is no filter or other impediment to cause clogging. In such case, obviously, no gas is withdrawn, however, the system can handle 100% liquid without disrupting its function once gas again is present.

In the preferred embodiment, used to measure gases in a patient's exhalation, it has been found that an expanded PTFE conduit 12 having an internal diameter of about 1.0 mm. and a wall thickness of about 0.5 mm. is usable having a pore size of about 1.5 microns and a porosity of about 50%. Such conduit is commercially available from W. L. Gore & Associates. Its length is preferably from about 19.32 mm. to about 38.1 mm. and has been found to acceptably be used with a flow of about 100.0 cc/min. of exhalation entering inlet 14 and a differential pressure across the wall of conduit 12 of about 0.5 in. Hg. It should be pointed out, that, if conduit 12 is shorter than about 14.7 mm., it clogs quickly in a clinical setting. If, however, the conduit 12 is longer than about 44.1 mm., an unacceptable wave form degradation occurs. It should be mentioned that the flow rate of about 100 cc/min. is particularly critical for the measuring of $CO_2$ levels in breath gas because higher flow rates are not considered to be safe for children and infants.

As noted, one can readily balance the flow of dry gas from gas outlet 20 and liquid from outlet 16 by adjusting pressure differentials between the inlet and outlet of the liquid/gas separator 10 and across the gas permeable wall material such that other pore sizes may be selected and other liquid/gas mixtures encountered. Typically, in the preferred embodiment, mentioned above, the flow rate of liquid is about 10% of that of the dry breath gas.

If conduit 12 contacts the inner surface of jacket 18, then, the effective length of conduit 12 is reduced; and in fact, may be reduced to a point that conduit 12 begins to clog. For instance, when the patient exhales, conduit 12 radially expands; and if the inner diameter of jacket 18 is equal to that of radially expanded conduit 12, then, conduit 12 will contact the inner surface of jacket 18. A possible additional source of contact arises from PTFE tubing being normally wound about a spool for sale and/or storage. When unwound from the spool, the PTFE tubing tends to have a pre-existing curvature. If the cut PTFE tubing is simply installed in jacket 18, then the conduit 12 formed by such cut PTFE will contact the inside surface of jacket 18.

However, as the inner diameter of jacket 18 increases, the possibility of the formation of dead air space in annular chamber 24 also increases. The greater the dead air space, the greater the wave form degradation because there is more space for dry gas to mix from one exhalation to the next. Therefore, in the present invention, jacket 18 has a minimum inner diameter sufficient to allow the radially expanded conduit 12 to clear its inner surface and, thus, prevent obstruction of annular chamber 24 by minimum dead air space surrounding conduit 12. Moreover, since the inner diameter of jacket 18 is at a minimum, the volume of annular chamber 24 is minimized to resist the formation of dead air space within chamber 24. Preferably, the inner diameter of jacket 18 is about 2.5 mm. so that annular chamber 24 has a thickness of about 0.25 mm.

In order to prevent contact between the inside surface of jacket 18 and conduit 12 caused by a pre-existing curvature in the tubing forming conduit 12, conduit 12 is subjected to a tensile preload force prior to and during the hardening of, for instance, the epoxy, forming potting material 22. Thus, potting material 22, in addition to its sealing function, may also serve to maintain the tensile preload force on conduit 12. The amount of preload force should be of sufficient magnitude to eliminate any pre-existing curvature in conduit 12. However, conduit 12 should not be stretched to the extent that pore size is altered.

While the invention has been disclosed and described with reference to a single embodiment, it will be apparent the variations and modifications may be made therein, and it is therefore intended in the following claims to cover each such variation and modification as falls within the true spirit and scope of the invention.

We claim:

1. A water separator to remove liquid and thereby to draw dry gas from a patient's exhalation for analysis of the dry gas in a gas analyzer, said water separator comprising:

means having an inlet for receiving the patient's exhalation, a liquid outlet for discharging the liquid removed from the patient's exhalation, and a conduit comprising a tubing communicating between said inlet and said liquid outlet and formed of a porous material permeable to the dry gas, but impermeable to the liquid for allowing the dry gas to pass through said porous material and for causing the liquid to remain within said conduit for discharge through said liquid outlet;

chamber means having an inner surface forming a cylindrical, annular chamber around said conduit for collecting the dry gas passed through said porous material and a gas outlet in communication with said cylindrical chamber for discharging the dry gas to the gas analyzer;

said conduit subject to radial expansion upon the patient's exhalation;

said annular chamber having a predetermined, minimum inner diameter sufficient to allow said conduit to expand without contact between said conduit and said inner surface of said chamber means for preventing obstruction of said annular chamber by said conduit and for minimizing the volume of said annular chamber to resist the formation of dead air spaces in said annular chamber;

means for sealing the ends of said annular chamber around said conduit means;

means establishing a negative pressure differential between said annular chamber and the inside of said conduit means for drawing the dry gas through said porous material and out of said gas outlet; and means establishing a negative pressure differential between said liquid outlet, and said inlet for drawing the patient's exhalation into said inlet and for drawing the liquid out of said liquid outlet.

2. The water separator of claim 1 wherein:

said conduit has a pre-existing curvature and an applied tensile preload force to eliminate said pre-existing curvature, thereby to insure said conduit remains clear of said inner surface; and said sealing means maintains said tensile preload force on said conduit.

3. The water separator of claim 2 wherein:

said chamber means comprises a cylindrical tube-like jacket; and said inlet and said liquid outlet comprise a pair of end tubes tightly fitted within the ends of said conduit and protruding from the ends of said jacket;

said sealing means comprises a potting material formed of an epoxy bonding said end tubes to said jacket.

4. The water separator of claim 1 wherein:

said conduit is formed of a polytetrafluoroethylene tube having a plurality of pores of about 1.5 microns in diameter, a porosity of about 50 percent, an inner diameter of about 1.0 millimeters, an outer diameter of about 2.0 millimeters, a length of between about 19.32 millimeters and about 38.1 millimeters;

said predetermined minimum diameter of said annular chamber is about 2.5 millimeters.

said negative pressure differential is equal to about 0.5 in. Hg.; and said patient's exhalation is drawn into said inlet at about 100.0 cc./min.

* * * * *